United States Patent [19]

Hare et al.

[11] 4,290,893

[45] Sep. 22, 1981

[54] SEPARATION OF AMINO ACIDS BY LIQUID CHROMATOGRAPHY USING CHIRAL ELUANTS

[75] Inventors: P. Edgar Hare, Adelphi, Md.; E. Gil-Av, Rehovot, Israel

[73] Assignee: Yeda Research & Development Co. Ltd., Rehovot, Israel

[21] Appl. No.: 48,422

[22] Filed: Jun. 14, 1979

Related U.S. Application Data

[63] Continuation-in-part of Ser. No. 37,061, May 8, 1979.

[51] Int. Cl.$^3$ ............................................. B01B 15/08
[52] U.S. Cl. .................................. 210/656; 210/198.2
[58] Field of Search .................... 210/31 C, 656, 198.2

[56] References Cited

U.S. PATENT DOCUMENTS 4,133,753  1/1979  Takbuchi .......................... 210/31 C

OTHER PUBLICATIONS

Separation of Phenolic Compounds by Anion Exchange Resin in Copper Chloride (11) Organic Solvent System by Lee et al., Analytical Chem. vol. 45, No. 2, 2/1973, pp. 396-399.
Resolution of the Optical Isomers of Dansyl Amino Acids by Reverse Phase Liquid Chromatography with Optically Active Metal Chelate Additives by Page et al., Analytical Chemistry, vol. 51, No. 3, 3/1979, pp. 433-435.
Resolution of Optical Isomers by Liquid Chromatography by Pirkle et al. Journal of Chromatography, 123 (1976), pp. 400-404.
Chromatographic Study of Optical Resolution by Nakazawa et al., Journal of Chromatography 160 (1978) pp. 89-99.
Ligand Chromatography and the Preparation of Optically Active Compounds by Davankov in Soviet Science Review, vol. 3, No. 6, Nov. 1972, pp. 352-356.
Davankov, V.A. et al. "Ligand-Exchange Chromatography of Racemates; VI. Separation of Optical Isomers of Aminoacids on Polystyrene Resin Containing L-proline or L-azetidine Carboxylic Acid," *J. Chrom.*, 155 (2) 295-302, 1978.
Gil-Av, E. et al. "Resolution of Underivatized Aminoacids by Reversed-Phase Chromatography," *J. Am. Chem. Soc.*, 102, 5115-5117 (1980).

*Primary Examiner*—John Adee
*Attorney, Agent, or Firm*—Browdy and Neimark

[57] ABSTRACT

An aqueous eluant containing a chiral ligand and a suitable metal ion effects the separation of enantiomers on a non-chiral support. The stereoselectivity is ascribed to differences in stability and/or different partition coefficient of the diastereomeric inner sphere complex formed in solution.

11 Claims, 1 Drawing Figure

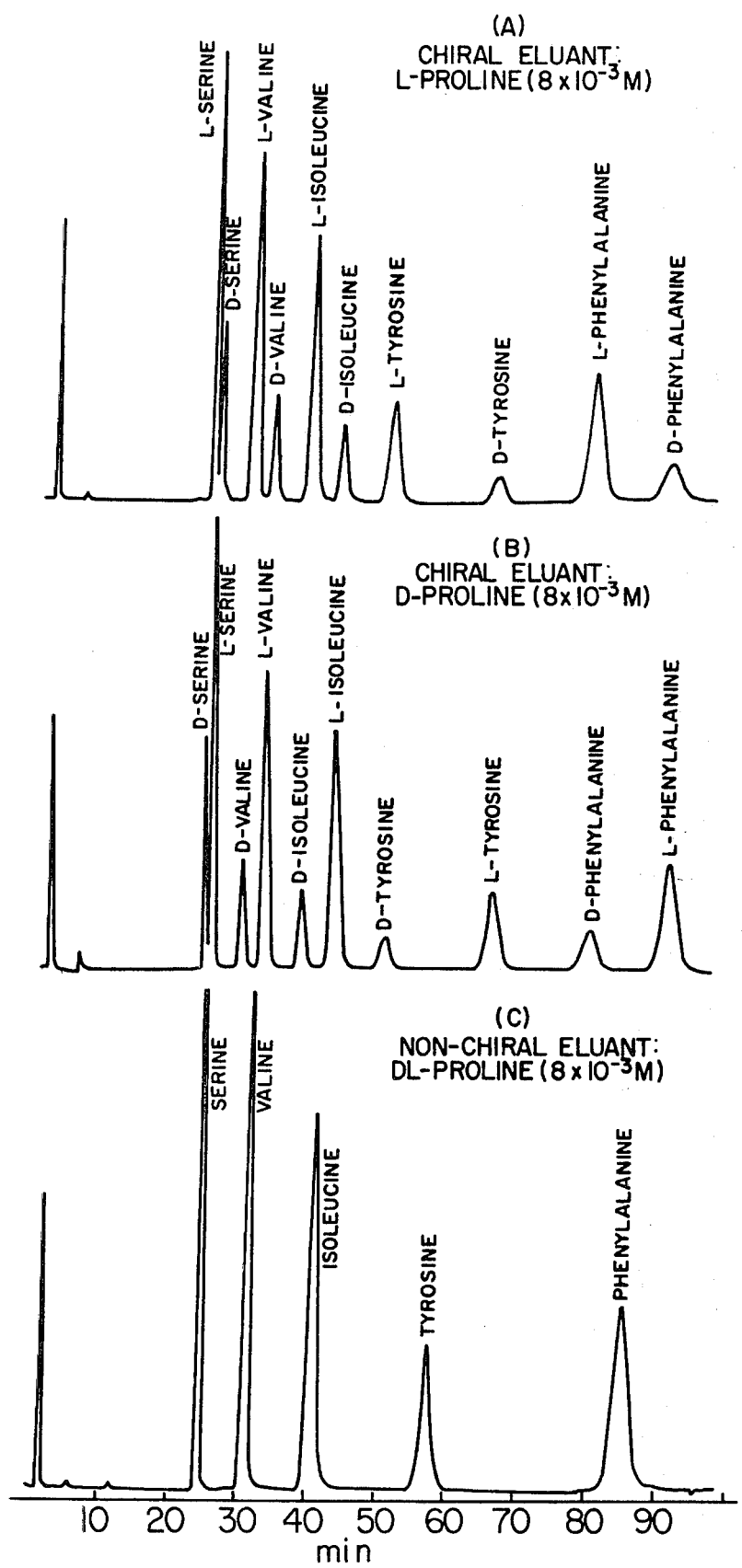

SEPARATION OF AMINO ACIDS BY LIQUID CHROMATOGRAPHY USING CHIRAL ELUANTS

CROSS REFERENCE TO RELATED APPLICATION

This appln. is a continuation-in-part of Ser. No. 037,061, May 8, 1979.

BACKGROUND OF THE INVENTION

1. Field of the Invention

The present invention relates to the separation of enantiomers.

2. Description of the Prior Art

Enantiomers are mirror-image isomers of the same compound with identical physical properties except that they rotate the plane of polarized light in opposite directions. Enantiomers also have identical chemical properties except toward chiral (optically active) reagents.

Chromatographic resolution of optical isomers requires the introduction of an asymmetric environment either intramolecularly, by conversion to diastereomers, or intermolecularly, by the use of chiral stationary or mobile phases. In gas chromatography, excellent resolution of derivatized amino acids has been achieved via diastereomers (R. Charles, G. Fischer, E. Gil-av, *Israel J. Chem.* 1, 234 (1963); G. E. Pollock, V. I. Oyama, R. D. Johnson, *J. Gas Chromatogr.* 3, 174 (1965)), as well as with chiral stationary phases. N-lauroyl-L-valine t-butylamide is an example of a useful chiral stationary phase. (B. Feibush, *Chem. Commun.* 544 (1971); R. Charles, U. Beitler, B. Fiebush, E. Gil-Av, *J. Chromatogr.* 112, 121 (1975). See also H. Frank, G. J. Nicholson, E. Bayer, *J. Chromatogr. Sci.* 15, 174 (1977).) Similarly in liquid chromatography, both these approaches have led to good separations, e.g. of diastereomeric dipeptides (J. M. Manning and S. Moore *J. Biol. Chem.* 243, 5591 (1968); F. Mikes, G. Boshart, E. Gil-Av, *J. Chromatogr.* 112,205 (1976)); and H. Numan, R. Helder, H. Wynberg,) *Recueil* 95, 211 (1976)) have resolved helicenes on optically active supports.

In contrast, the effect of chiral eluants has not been extensively investigated and has been described in only a few publications e.g.; W. H. Pirkle and D. L. Sikkenga, *J. Chromatogr.* 123, 400 (1976); and H. Nakazawa and H. Yoneda, ibid. 160, 89 (1978) and references therein. Le Page et al. (*Anal. Chem.* 51:433 (1979)) have recently separated dansyl derivatives of amino acids by reverse phase liquid chromotography using a chiral eluant. They use a chiral diethylenetriamine ligand coordinated to zinc dissolved in the eluant and have shown the separation of several pairs of derivatized enantiomers. In contrast, in the present system it is unnecessary to derivatize the enantiomers.

SUMMARY OF THE INVENTION

It has been discovered that aqueous eluants containing chiral ligands and a suitable metal ion effect the separation of enantiomers capable of forming diastereometric inner sphere coordination complexes of differential stability and/or different partition coefficient, while operating with a non-chiral support. The relative stabilities and kinetics of reversible formation of the diastereomeric complexes in the mobile phase must be such as to be appropriate for the chromatographic process. Most especially, the invention permits one to separate underivatized enantiomers such as α-amino acids.

DESCRIPTION OF THE DRAWING

The FIGURES illustrate the effect of the chirality of the eluant on the separation of D- and L-amino acid enantiomers by ligand-exchange chromatography. The vertical axis illustrates relative fluorescense while the horizontal axis represents time, in minutes.

DESCRIPTION OF PREFERRED EMBODIMENTS

In broad aspects, an aqueous eluant containing a chiral ligand and a suitable metal ion capable of forming diastereomeric inner sphere complexes of differential stability and/or different partition coefficient with the enantiomers of the compounds to be resolved effects separation on a non-chiral support. Most especially, underivatized enantiomers can be resolved by this procedure.

The present invention finds particularly preferred use when the non-chiral support is an ion exchange column, as illustrated in Examples 1 and 2. The present invention is not limited to ion-exchange columns, of course, and other separation procedures can be used, for example, reversed phase separation.

For purposes of illustration, the following discussion will often be in the context of underivatized amino acid enantiomers since the present invention finds particular application therewith. For example, for detection and quantification of picomole amounts of amino acids, the eluant can be monitored for fluorescence after reaction with, e.g., o-phthalaldehyde, or another reagent insensitive to complex components but highly sensitive for amino acids containing a primary amino group.

In this regard, it is to be again emphasized that the present invention finds particular usage with underivatized enantiomers in general since such are much simpler to use than, for example, complex derivatized enantiomers as used in the prior art. While it is highly preferred to use underivatized enantiomers, the present invention can be applied, though this is not preferred, to derivatized enantiomers such as, for example, methylated or acetylated enantiomers.

The present invention thus provides a surprisingly simple procedure that results in the separation of a considerable number of enantiomers, particularly α-amino acid enantiomers, without the need for prior derivatization.

The method is based on the addition of a chiral compound, e.g., a metal cation-amino acid complex to the eluant of a non-chiral support, e.g., a cation-exchange column. In one specific application which will hereafter be used as illustrative, but which is not to be taken as limitative, $Cu^{2+}$ proline complexes are dissolved (molar ratio $Cu^{2+}$/proline is $\frac{1}{2}$) in a sodium acetate buffer. After the column is equilibrated, an amino acid sample is injected and is resolved into its enantiomers as shown in the FIGURE. Equilibration of the ion-exchange column to the copper form requires several hours unless the resin is converted to the copper form before the column is packed. Once equilibrated with copper the various eluants can be interchanged with minimal reequilibration as long as the copper-ion concentration is not altered.

The chromatographic system on which the process was carried out had been developed previously for the rapid, highly sensitive ion-exchange analysis of amino acids using 5 μm bead resins; it is described in detail by P. E. Hare, in *Methods in Enzymology*, Vol. 47, *Enzyme Structure*, Part E, C. H. W. Hirs and S. N. Timasheff, Eds. (Academic Press, New York, 1977), pp. 3–18. Dionex Corporation offers an amino acid analyzer kit patterned after the system described above. Separation was monitored by fluorometry in a conventional manner using a Fluoro-monitor (Aminco catalog No. J4-7461) and a prototype of an Auxiliary Fluro-monitor (Aminco catalog No. J4-7502) after post-column reaction of the eluant with o-phthalaldehyde as described in M. Roth, *Anal. Chem.* 43, 880 (1971); J. R. Benson and P. E. Hare, *Proc. Natl. Acad. Sci. U.S.A.* 72, 619 (1975). To prevent precipitation of copper compounds by the o-phthalaldehyde solution, EDTA was added to the reagent (2.5 g/liter). o-Phthalaldehyde does interact with primary but not with secondary amines, so that proline does not interfere (nor does $Cu^{2+}$). Because of these circumstances the resolutions reported could be observed. The method is sensitive to picomole amounts.

The aromatic amino acids show particularly efficient separation. For the tyrosine enantiomers, e.g., the separation factor (r=ratio of the adjusted retention times of the second peak over those of the first peak) equals 1.28 with a 0.1 N sodium acetate buffer at pH 5.5, and 1.33 with 0.05 N sodium acetate at the same pH (FIG. 1). On a 3-cm column complete resolution of tyrosine could be obtained in 5 minutes. At least some of the enantiomer pairs listed in Table 1 with separation factors of 1.00, indicating no resolution, can in fact be separated under different operating parameters. We have, for instance, found the D,L-asparagine, which has r=1.00 under the conditions of Table 1, shows partial resolution at lower ionic strength and pH.

Our results also indicate that temperature affects the process of the present invention. Thus, D,L-valine gives only one peak at 25° but base-line resolution at 75°. Similar observations have been seen in the prior art, see B. L. Lefebvre, R. Audebert, C. Quivoron, *Israel J. Chem.* 15, 69 (1967) and references therein; note also S. Rogozhin and V. Davankov, *J. Chem. Soc. D* 490 (1971) and references therein. Some caution in the use of higher temperatures must, however, be exercised, because of possible racemization during chromatography. Indeed, L-serine showed a slight but measurable increase in the D-enantiomer content when the column was operated at 90°, as compared with 60°. The temperature of operation is usually about 40° C. to about 90° C., more generally about 60° to about 75° C.

Many enantiomers can be resolved efficiently by adjusting the temperature, the pH, and the ionic strength. For example, basic amino acids such as lysine, histidine, and arginine, which do not emerge under the conditions of the Example, might be eluted in a reasonable time at higher ionic strength and/or on a shorter column.

Additional options for obtaining desired resolutions are the use of chiral ligands differing from proline, including other amino acids, their derivatives or other classes of compounds. Changing the nature of the cation also permits further resolution. For instance, under the conditions of the Examples γ-hydroxy-proline in conjunction with $Cu^{2+}$ shows stereoselectivity as good as or higher than that of proline. L-azetidine carboxylic acid was also found to be an effective resolving agent.

As seen from the Examples, when an L-proline ligand is used, the L-enantiomer of the amino acid resolved is eluted before the corresponding D-isomer. This order is reversed when a D-proline—copper complex is dissolved in the eluant (FIG. 1B), and there is no resolution with a racemic proline-copper complex in the eluant. Switching chirality of the eluant offers a useful method for distinguishing nonchiral artifacts from true enantiomers in a sample and requires only a few minutes for equilibrating the column. Retention times can be accurately reproduced, as seen in FIG. 1.

The stereoselectivity observed is ascribed to differences in the stability contants of diastereomeric species such as L-proline—$Cu^{2+}$—L-amino acid and the L-proline—$Cu^{2+}$—D-amino acid complexes in aqueous solution. Qualitative and quantitative reports on such differences have been published (see for example, B. L. Leach and R. J. Angelici, *J. Am. Chem. Soc.* 91, 6297 (1969)).

The process of the present invention thus provides a simple, automated procedure for quantitative enantiomer analysis with simultaneous determination of enantiomeric composition. Such a method will be most useful in checking synthetic and naturally occurring, biologically active peptides for the presence of enantiomeric components. For example, screening physiological fluids for D-amino acids has been handicapped in the past by the inavailability of a suitable automated technique. The discovery of increasing amounts of D-amino acid enantiomers in progressively older fossils, in certain living tissues such as tooth dentin and enamel, as well as in lens proteins of cataract patients, indicates other areas where the procedure would be very useful. Food nutrition studies, concerned with the dietary effect of the D-amino acid enantiomers, would also benefit from the method.

EXAMPLE 1

Identical aliquots of a mixture of five pairs of amino acid enantiomers, each consisting of 0.375 nanomole L-form and 0.125 nanomole D-form, were injected in each run. The amino acids are as shown in the FIGURE.

Sodium acetate buffer (0.05 N, pH 5.5) containing $4 \times 10^{-3}$ M $CuSO_4$ and $8 \times 10^{-3}$ M proline was used as eluant. The chirality of the proline ligand was as indicated in the FIGURE; while chirality is by L or D form, obviously for other non-amino acid compounds the enantiomers may be designated by "+" or "−" or "S" or "R" terminology. The column was equilibrated with each separate eluant for 15 minutes prior to sample injection. Ion exchange column: 12 cm long×0.2 cm I.D. fully packed with DC 4a resin (polystyrene resin; available from Dionex Corporation). Equilibration was determined when the Cu-proline complex saturated the ion exchange resin, i.e., Cu-proline complex passed through the column without change, whereafter separation was initiated). Eluant flow rate, 10 ml per hour; reagent flow rate, 10 ml per hour; column pressure, 200 bars; column temperature, 75° C. A dual Milton-Ray pump was used to deliver the eluant and reagent. Separation was complete in 90 minutes. The results are illustrated in the FIGURE where:

In (A) L-proline effected the separation of all five pairs of enantiomers with the L-enantiomers eluting before the corresponding D-enantiomers.

In (B) D-proline reversed the order of elution.

In (C) with racemic proline no resolution did, of course, occur; the amino acids eluted half way between the corresponding enantiomeric peaks in (A) and (B).

An ion exchange column is not mandatory; a further option is the use of a non-chiral support other than an ion exchange column, e.g., a reversed phase support as illustrated in Example 3.

EXAMPLE 2

Following the procedure of Example 1 except for doubling the concentration of buffer, copper and proline, the 18 pairs of amino acids in Table 1 were separated in 18 process runs. In all 18 runs separation was effected.

| Amino Acid | | $t'_R$ (min) | Separation Factor (r) |
|---|---|---|---|
| (Cysteic Acid) | | (0) | |
| Allothreonine | L | 10.0 | 1.14 |
| | D | 11.4 | |
| Serine | L | 12.9 | 1.04 |
| | D | 13.4 | |
| Threonine | L | 13.0 | 1.05 |
| | D | 13.7 | |
| α-Amino-n-Butyric Acid | L | 16.2 | 1.02 |
| | D | 16.6 | |
| Valine | L | 16.3 | 1.09 |
| | D | 17.7 | |
| Isoleucine | L | 21.5 | 1.10 |
| | D | 23.7 | |
| Norvaline | L | 21.5 | 1.04 |
| | D | 22.3 | |
| 3,4-Dihydroxyphenylalanine | L | 22.3 | 1.28 |
| | D | 28.5 | |
| Alloisoleucine | L | 23.5 | 1.09 |
| | D | 25.5 | |
| Methionine | L | 23.8 | 1.03 |
| | D | 24.6 | |
| Leucine | L | 28.3 | 1.01 |
| | D | 28.6 | |
| Ethionine | L | 29.0 | 1.04 |
| | D | 30.3 | |
| Norleucine | L | 30.8 | 1.05 |
| | D | 32.3 | |
| Tyrosine | L | 30.8 | 1.28 |
| | D | 39.4 | |
| m-Tyrosine | L | 34.1 | 1.21 |
| | D | 41.1 | |
| o-Tyrosine | L | 36.7 | 1.18 |
| | D | 43.2 | |
| Phenylalanine | L | 48.7 | 1.13 |
| | D | 55.0 | |
| p-Fluorophenylalanine | L | 64.0 | 1.18 |
| | D | 75.6 | |

EXAMPLE 3

Following the procedure of Example 1, except that instead of an ion exchange resin, 10μ silica particles to which an octadecyl residue was bonded (reversed phase) was packed in a column 25 cm length and 4.6 mm I.D. histidine was separated into its enantiomers at room temperature. The flow rate of the mobile phase was 1 ml/min. The separation factor was found to be 1.28. With the same column and under the same conditions, but using an aqueous eluant containing $8 \times 10^{-3}$ M CuSO$_4$.5H$_2$O, $16 \times 10^{-3}$ M L-proline and 0.025 N sodium acetate, the enantiomers of the following amino acids were separated: alanine, valine, leucine, isoleucine, alloisoleucine, methionine, allothreonine, phenylalanine, tyrosine, arginine, histidine, lysine, tryptophane, glutamic acid, and glutamine.

This list includes a number of compounds which so far could either not be resolved at all or only partially on ion exchange columns, e.g., alanine, leucine, arginine, histidine, lysine, tryptophane, glutamic acid, and glutamine. It should be mentioned that for valine a separation factor higher than 2.5 was found under these conditions. Another significant fact is that under these conditions, the order of emergence is, in general, the reverse of that observed for the ion exchange column suggesting that the mechanism of chiral recognition is distinct in the two cases.

While the above discussion has been specific to certain materials, conditions, etc., the present invention is not limited thereto but finds wide application.

For example, enantiomers in general can be separated including, but not limited to, carboxylic acids, amines, amino alcohols, carbohydrates, etc. Generally, enantiomers amenable to current liquid-solid phase separations are amenable to processing according to the present invention.

Similarly, while copper has been illustrated as the cation and proline as the amino acid used to form a complex, other cations and/or chiral complex forming organic ligands can be used, e.g.:

Cations: Mg, Ca, Fe, Co, Mn, Ni, Zn, Cd, Hg, etc. In this regard, Fe, Co, Mn, and Ni are more preferred cations used in accordance with the present invention, and Cu is the most preferred cation used in the present invention. To date, Zn appears to offer somewhat inferior results to these more preferred cations, when used with an ion exchange support.

Chiral complex forming organic ligands: amino acids or derivatives thereof, e.g., including but not limited to, proline peptides, hydroxylprolines, any amino acid derivatives where the amino group is blocked; chiral amines, carboxylic acids, amino sugars and carbohydrates, alkaloid bases, etc.

Furthermore, though analytical scale applications have been illustrated, the invention is not limited thereto but could be scaled up to the preparation of enantiomers.

The molar ratio of cation: organic ligand cannot be fixed since it will vary depending on the amount needed to form a complex. So long as a complex is formed in solution i.e., in the eluant, that is sufficient for the present invention.

The complex is usually dissolved in a conventional buffer for use. Sodium acetate has been illustrated, but other conventional buffers can be used, e.g., sodium or potassium formates, phosphates, etc. Furthermore, organic solvents miscible with water could be added.

It is most preferred in accordance with the present invention that the aqueous eluant not contain any organic solvent. This is one substantial benefit of the present invention, i.e., the present invention can be practiced with an essentially aqueous base system wherein more expensive and often noxious organic solvents need not be used. In certain instances, a solvent can be used if desired, but under most circumstances, a solvent will be used only if one does not utilize an ion-exchange resin as the non-chiral support. If one does utilize an organic solvent, generally no more than about 10 to 20 volume % of solvent, usually less than 10 volume %, based on the amount of water present in the aqueous eluant, will be used. This should be compared to prior art processes requiring large proportions of solvent.

While only one ion-exchange resin and reversed phase have been illustrated, other conventional ion-exchange resins or other chromatographic supports can be used and selected by applying conventional procedures in the art, e.g., silica gels, bonded silica gel, polyamides, celluloses, etc.

The temperature, pressure and time of operation can be widely varied. Of these factors, temperature, as earlier indicated, tends to be more important.

Pressure is sufficient to insure the eluant passes through the packed column.

Time cannot be specified; it is merely sufficient to insure substantially complete separation and can be determined in a conventional manner.

The absolute amount of eluant is determined in a conventional manner; the amount of chiral complex is sufficient to insure adequate separation and is conventionally determined in an empirical manner. The amounts in the Examples are, based on present knowledge, close to optimum.

One additional point is worth noting: while a post-separation fluorescence reaction with o-phthalaldehyde has been described, this is not mandatory in the present invention, though such a reaction or its equivalent can be practical in a conventional manner.

One further substantial benefit of the present invention is that it can be utilized with natural, as opposed to synthesized, chiral ligands. This is an important advantage because many prior art processes require synthetic ligands. In one highly preferred embodiment of the present invention, a simple yet versatile system is provided wherein a solid ion-exchange column is utilized in combination with an aqueous system, i.e., an aqueous eluant containing less than about 10 volume % organic solvent(s), preferably no organic solvent(s).

Such a system can be used to separate underivatized enantiomers in a simple fashion, utilizing natural, as opposed to synthesized, ligands.

While the invention has been described in detail and with reference to specific embodiments thereof, it will be apparent to one skilled in the art that various changes and modifications can be made therein without departing from the spirit ahd scope thereof.

What is claimed is:

1. A process for separating enantiomers which comprises contacting the same on a solid non-chiral chromatographic support, with an aqueous solution containing less than about 10 volume % organic solvent, and containing a chiral ligand and a suitable metal ion capable of forming with the enantiomers inner sphere complexes of different stability and/or different partition coefficient.

2. A process for separating enantiomers which comprises contacting the same, on a solid non-chiral chromatographic support, with an aqueous solution containing a naturally occurring chiral ligand and a suitable metal ion capable of forming with the enantiomers inner sphere complexes of different stability and/or different partition coefficient.

3. A process for separating underivatized enantiomers which comprises contacting the same on a solid non-chiral chromatographic support, with an aqueous solution containing less than about 10 volume % organic solvent, and containing a chiral ligand and a suitable metal ion capable of forming with the enantiomers inner sphere complexes of different stability and/or different partition coefficient.

4. A process for separating enantiomers which comprises contacting the same, on a solid non-chiral chromatographic ion exchange column, with an aqueous solution containing a chiral ligand and a suitable metal ion capable of forming with the enantiomers inner sphere complexes of differential stability and/or different partition coefficient.

5. A process for separating enantiomers which comprises contacting the same on a solid non-chiral reversed phase chromatographic support, with a aqueous solution containing a chiral ligand and a suitable metal ion capable of forming with the enantiomers inner sphere complexes of different stability and/or different partition coefficient.

6. In a process for preparing enantiomers the improvement which comprises the separation of the optical isomers by contacting them, on a solid non-chiral chromatographic support, with an aqueous solution containing less than about 10 to 20 volume % of organic solvent, and containing a chiral ligand and a suitable metal ion capable of forming with the enantiomers inner sphere complexes of different stability and/or different partition coefficient.

7. A process in accordance with claim 5, wherein said non-chiral reversed phase support comprises silica gel to which an octadecyl residue is linked covalently.

8. A process in accordance with one of claims 2, 4 or 5, wherein said enantiomers are underivatized.

9. A process in accordance with one of claims 1 to 5, wherein said chiral ligand and metal ion comprise a metal ion-L- or D-amino acid complex.

10. A process in accordance with one of claims 2, 4 or 5, wherein said aqueous solution contains less than about 10–20 volume percent of organic solvent.

11. A process in accordance with one of claims 1, 3, 4, or 5, wherein said chiral ligand is a naturally occurring chiral ligand.

* * * * *